(12) United States Patent
Alasri et al.

(10) Patent No.: US 8,933,128 B2
(45) Date of Patent: Jan. 13, 2015

(54) USE OF A COMPOSITION FOR TREATING THE SURFACES OF LIVESTOCK BUILDINGS AND/OR THE MATERIAL THEREIN

(75) Inventors: Richard Alasri, Ieper (BE); Koen Brutsaert, Ieper (BE)

(73) Assignee: CID Lines N.V., Ieper (BE)

( * ) Notice: Subject to any disclaimer, the term of this patent is extended or adjusted under 35 U.S.C. 154(b) by 631 days.

(21) Appl. No.: 12/865,491

(22) PCT Filed: Feb. 5, 2009

(86) PCT No.: PCT/EP2009/000789
§ 371 (c)(1),
(2), (4) Date: Sep. 9, 2010

(87) PCT Pub. No.: WO2009/098054
PCT Pub. Date: Aug. 13, 2009

(65) Prior Publication Data
US 2011/0039941 A1 Feb. 17, 2011

(30) Foreign Application Priority Data
Feb. 5, 2008 (FR) ...................................... 08 00577

(51) Int. Cl.
| *A01N 33/12* | (2006.01) |
| *A01N 25/00* | (2006.01) |
| *A01N 25/32* | (2006.01) |
| *A01P 15/00* | (2006.01) |
| *A01N 33/02* | (2006.01) |

(52) U.S. Cl.
CPC ..................................... *A01N 33/02* (2013.01)
USPC ............ 514/642; 514/643; 424/405; 424/406

(58) Field of Classification Search
CPC .... A01N 33/02; A01N 2300/00; A01N 33/12
USPC ........................... 514/643, 642; 424/405, 406
See application file for complete search history.

(56) References Cited

U.S. PATENT DOCUMENTS

| 4,185,098 A | * | 1/1980 | Cuntze et al. ................... 514/77 |
| 5,585,403 A | | 12/1996 | Seki et al. |
| 2003/0228373 A1 | * | 12/2003 | Ludensky et al. ............. 424/600 |

FOREIGN PATENT DOCUMENTS

| BE | 1016296 A3 | 7/2006 |
| EP | 0397220 A | 11/1990 |
| FR | 2347935 A | 11/1977 |
| WO | 02/23990 A | 3/2002 |

OTHER PUBLICATIONS

Derwent Abstract for BE 1016296 A3.*
Guimaraes Jose S Jr et al: "In vitro evaluation of the disinfection efficacy on *Eimeria tenella*, unsporulated oocysts isolated from broilers" Revista Brasileira De Parasitologia Veterinaria, Apr. 2007, p. 67-71, vol. 16, No. 2, Brazil J. Vet. Parasitol.

* cited by examiner

*Primary Examiner* — Sreeni Padmanabhan
*Assistant Examiner* — Jody Karol
(74) *Attorney, Agent, or Firm* — McAndrews, Held & Malloy Ltd.

(57) ABSTRACT

The invention relates to the use of a composition for treating the surfaces of livestock buildings and/or the material therein in order to eliminate and/or inhibit pathogenic protozoa, and in particular coccidiosis oocysts. According to the invention, said composition essentially comprises the combination of an alkylamine and of a quaternary ammonium or of a quaternary ammonium derivative.

4 Claims, 1 Drawing Sheet

|  | Infection Dose | Excreted Dose |
|---|---|---|
| control 31 | 31 | 68613.26 |
| control 40 | 40 | 0 |
| control 62 | 62 | 115601.85 |
| control 250 | 250 | 1549042.5 |

|  | Excreted Dose | Corresponding infection dose | Infection Ratio | Efficiency Ratio |
|---|---|---|---|---|
| Phenol-based market product | 292023.6 | 76 | 3.8% | 96.2% |
| Composition 1 | 5859.6 | 36 | 1.8% | 98.2% |

USE OF A COMPOSITION FOR TREATING THE SURFACES OF LIVESTOCK BUILDINGS AND/OR THE MATERIAL THEREIN

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

This invention concerns the use of a composition for treating the surfaces of livestock buildings and/or the material therein so as to eliminate and/or inhibit pathogenic protozoa and in particular coccidiosis oocysts.

2. Description of Related Art Including Information Disclosed Under 37 CFR 1.97 and 37 CFR 1.98.

Coccidiosis is an infection caused by single-cell organisms. These organisms belong to the class of protozoa and they are called oocysts most often. Oocysts, so-called non-sporulated are excreted by animals in their stool. They remain in the environment and sporulate. These sporulated oocysts, if ingested, cause a diarrhea and sometimes animals' death.

When it comes to fighting against animals' coccidiosis, antibiotics, oocyst development inhibitor molecules are commonly used: coccidiostatics.

There are few dilute solutions, to be applied in the animals' environment for destroying oocysts. Generally, these solutions contain compounds, such as phenols, chloroform and/or ammonia. German document DE-10 222 455 describes, for example, the use of a phenol-combined ester having an action against oocysts.

The use of alkylamine for preventing the proliferation of animal parasites, and more particularly of the following parasites, is also known from document BE-101 6296: *Ornithonyssus Sylvarium, Ornithonyssus Bursa*, pigeon *Argas* and more particularly *Dermanyssus Gallinae* (chicken red louse).

A disinfectant for the elimination of parasites and in particular coccidiosis oocysts is also known from document EP 0 397 220, comprising: one or more active disinfectants belonging to the group of aliphatic alcohols with 1 to 4 carbon atoms, and one or more surfactants and water.

The preferred surfactants are of anionic type (RSO3-), and more particularly:
  (formula I) a sulfo-ester (COOR2) of fatty acids (R1) with R1 being a vegetable fatty acid and R2 a C1 to C4 chain.
  (formula II) an ethoxylated or propoxylated fatty alcohol, a slightly foaming surfactant of the block copolymer family with:
    R3_O: fatty alcohol portion.
    If R4=H, an ethoxylated fatty alcohol since (CH2_CH0) is the monomer (2C)-m which defines the polymer.
    If R4=CH3, a propoxylated fatty alcohol since (CH2-C(HO)—CH3) is the monomer (3C)-m which defines the polymer.
  (formula III) a polyethoxylated fatty alcohol also called alcohol polyether. Possibly, the surfactant can include fettamine and a quaternary ammonium in one of its branches.

Document FR 2.347.935 concerns a disinfectant which is useable against protozoa oocysts, and in particular resistant forms of various coccidia species. Document FR 2.2347.935 suggests the following mixture of a non-conventional quaternary ammonium which may be summed up as a dialkyl (alkyl/acyl/trialkylamino) quaternary ammonium of a phosphoric ether (I), a 70-90% chlorinated (chlorinated hydrocarbon) aliphatic or aromatic solvent, a polyethoxylated (non-ionic) tertiary di-amine alkyl (III), an amphoteric surfactant, alkyl (hydroxy), possibly an imidazoline (IV) and an anionic and/or non-ionic emulsifying agent (emulsifying and solubilising of the 1-3-4 into 2) in significant proportion for solubilisation in water.

This formula is relatively non-polar with a lot of chlorinated solvent, the dilution used is 0.25 to 10% in water. Imidazoline keeps the aqueous dilution stable with little polar formula.

Document FR2347935 describes the power against coccidia that could be thought of as dissolution of the keratin- and lipid-containing shells. To that end, the power of the chlorinated solvent is put in evidence.

Document U.S. Pat. No. 5,585,403 provides a disinfectant composition comprising one quaternary ammonium combined with one conventional dichlorobenzene having an activity against coccidiosis oocysts. This 1:400 diluted composition is applied in the habitat of the infected animals. It is a chlorinated compound having an action against coccidia.

The article "*In vitro evaluation of the disinfection efficacy on Eimeria tenella, unsporulated oocysts isolated from broilers*" by José GUIMARAES dated 2007, is based on a study of sporulation inhibition of nine disinfectants. The results of this study show that the disinfectants composed of sodium dodecyl benzene sulfonate, sodium hypochlorite with one orthodichlorobenzene and xylene associated with glycine compounds are with more than 60% efficient in the oocysts sporulation inhibition. Disinfectants solely based on quaternary ammonium (formula T1) do not appear sufficiently active to inhibit the oocysts sporulation.

The quaternary ammonium based formulae tested during that study are 1:1000 diluted, equivalent to 0.001%, with a 30 min contact time. By way of comparison in the official German protocol of the DVG (and of its guidelines 2000: "Guidelines for the testing of chemical disinfectants against coccida oocysts"), the tested formulae are 4% diluted with a 2 hour contact time.

The test protocol of this article measures the capacity of the disinfectants to inhibit the oocysts sporulation whereas the DVG protocole measures the reduction of the number of oocysts once inside the animal.

Document WO 02/23990 concerns a disinfectant, comprising an amine and/or a quaternary ammonium for the cleaning and the disinfection of the material, instruments, hands, chemical toilets and building materials among others. The disinfection comprises the bactericidal and fungicide activities.

BRIEF SUMMARY OF THE INVENTION

The present invention aims to propose an alternative to all the products applied to the animals' environment to fight against coccidiosis, enabling in particular perfect integration in a global safety program.

Particularly, the composition according to the invention essentially comprises the combination of an alkylamine and of a quaternary ammonium or of a quaternary ammonium derivative. It will find a particular application to eliminate and/or inhibit the stain of chicken *Eimeria tenella* oocysts.

By applying this composition on the surfaces, such as walls, floors and ceilings and the equipment of the buildings infected with coccidiosis oocysts, the applicant has surprisingly observed a reduction of the infection at least equivalent to that noticed when using products intended for said application, such as phenol products.

BRIEF DESCRIPTION OF THE DRAWINGS

The present invention will be understood better when reading the following description accompanied by the appended drawings wherein.

DETAILED DESCRIPTION OF THE INVENTION

Figures 1, 2, 3:
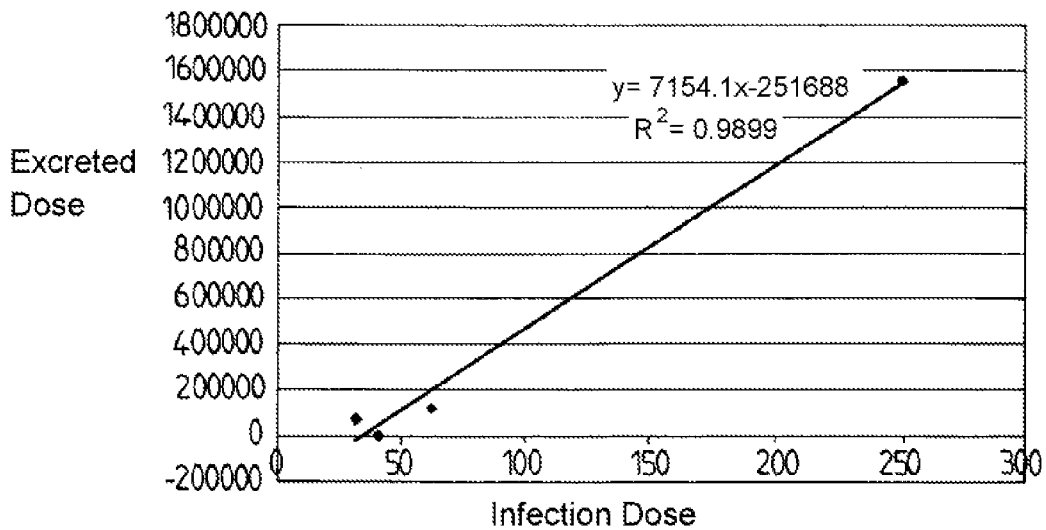
FIG. 1 is a table of the count results of the controls when applying the DVG German protocol.
FIG. 2 is a comparative table between a disinfectant according to the invention (composition 1) and a phenol-based commercial product.
FIG. 3 is a graphic representation of the results of the table of FIG. 1 as well as of the linear regression graph associated with these results.

This invention hence concerns the use of a composition for treating the surfaces of livestock buildings and/or the material therein so as to eliminate and/or inhibit pathogenic protozoa and in particular coccidiosis oocysts.

According to the invention, said composition essentially comprises the combination of an alkylamine and of a quaternary ammonium or of a quaternary ammonium derivative.

The composition may be applied by pulverization, thermonebulisation and/or soaking of the surfaces of livestock buildings and/or the material therein.

Said composition may be used for its sporicidal and/or keratolytic activity. More particularly, the composition may contain at least one alkylamine conferring the composition its keratolytic property. To that end, the alkylamine may be a triamine.

The alkylamine may be selected among the following group: dodecylamine, octadecylamine, N-tallow-amine, oleylamine, C-16-22-alkylamine, hexadecyl-dimethylamine, cocodimethylamine, oleyldimethylamine, dicocomethylamine, dodecyl-methylamine, cocopropylenediamine, C16-22-alkylpropylenediamine, oleylpropylenediamine, N-tallow-propylenediamine, cocopropylenediamine, oleyldipropylenetriamine, N-tallow-dipropylenetriamine, N-dodecyl-dipropylenetriamine, N-tallow-dipropylenetetramine, said list being non-exhaustive.

According to the invention the composition includes a biocide agent. More particularly, this biocide agent is a quaternary ammonium, or a quaternary ammonium derivative, providing the composition with a surfacting and disinfectant property.

The quaternary ammonium or quaternary ammonium derivative is selected among the following group:

compounds of the quaternary ammonium ion, (hydrogenated tallow alkyls) trimethyls, chlorides, compounds of the quaternary ammonium ion, coco trimethyl alkyls, chlorides, compounds of the quaternary ammonium ion, coco bis (hydroxyethyl)benzyl alkyl, chlorides, compounds of the quaternary ammonium ion, coco dimethyl benzyl alkyl, chlorides, compounds of the quaternary ammonium ion, coco dimethyl dialkyls, chlorides, compounds of the quaternary ammonium ion, bis(hydrogenated tallow alkyls) dimethyls, chlorides, compounds of the quaternary ammonium ion, soya trimethyl alkyls, chlorides, compounds of the quaternary ammonium ion, benzyl C8-18 alkyl dimethyls, chlorides, compounds of the quaternary ammonium ion, benzyl C12-18 alkyl dimethyls, chlorides, compounds of the quaternary ammonium ion, C6-12 dialkyl dimethyls, chlorides, compounds of the quaternary ammonium ion, benzyl C8-16 alkyl dimethyls, chlorides, compounds of the quaternary ammonium ion, benzyl C12-16 alkyl dimethyls, chlorides, compounds of the quaternary ammonium ion, C8-10 dialkyl dimethyls, chlorides, compounds of the quaternary ammonium ion, (oxydiethanediyl-1,2)bis[coco alkyldimethyl], dichlorides, compounds of the quaternary ammonium ion, C12-18 alkyl [(ethylphenyl)methyl]dimethyls, chlorides, compounds of the quaternary ammonium ion, benzyl C10-16 alkyl dimethyls, chlorides, compounds of the quaternary ammonium ion, benzyl C12-18 alkyl dimethyls, salt with benzisothiazol-1,2 one-3 (2H) (1:1), dioxide-1,1, compounds of the quaternary ammonium ion, C8-18 dialkyl dimethyls, chlorides, compounds of the quaternary ammonium ion, benzyl C12-14 alkyl dimethyls, chlorides, compounds of the quaternary ammonium ion, C12-14 alkyl [(ethylphenyl)methyl]dimethyls, chlorides, compounds of the quaternary ammonium ion, benzyl C8-18 alkyl dimethyls, bromides, compounds of the quaternary ammonium ion, [[[[(carboxy-2 ethyl)(hydroxy-2 ethyl)amino]-2 ethyl] amino]-2 oxo-2 ethyl]coco dimethyl alkyls, hydroxides, internal salts, N-methylmethanamine polymer (Einecs 204-697-4 with (chloromethyl)oxirane (Einecs 203-439-8)/polymerised quaternary ammonium chloride, quaternary ammonium iodides, quaternary ammonium compounds (benzylakyldimethyl (saturated and unsaturated C8-C22 alkyls, and soot alkyl, coco alkyl and soya alkyl) chlorides, bromides or hydroxides/BKC, quaternary ammonium compounds (dialkyldimethyl (saturated and unsaturated C6-C18 alkyls, and sulphur alkyl, coco alkyl and soya alkyl) chlorides, bromides or methyl sulfates/DDAC quaternary ammonium compounds (alkyltrimethyl (saturated and unsaturated C8-C18 alkyls, and sulphur alkyl, coco alkyl and soya alkyl) chlorides, bromides or methyl sulfates/TMAC, The quaternary ammonium derivative may be in particular an N-alkyl-N-benzyl-N,N-dimethylammonium salt of general formula:

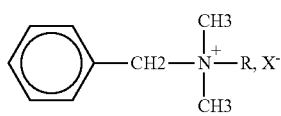

wherein R represents an alkyl chain having 8 to 18 carbon atoms and X being a counter-ion, such as for example a chloride, phosphate or acetate ion.

According to an embodiment, said composition may contain a surfactant, modifying the surface tension between two surfaces. Surfactants are amphiphilic molecules having two portions of different polarity, one lipophilic and the other one hydrophilic and polar. The incorporation of one or several surfactant into the composition allows promoting the dissolution of the ingredients of the composition and promoting the dissolution of the composition so as to obtain the ready-to-use solution. By way of non limiting example, the surfactant is an ethoxylated alcohol of C12-C15+11 E.O type.

According to an embodiment, the composition may contain one or several sequestering agents, having the property of forming complex bonds with the ions and thereby of limiting the harmful effect of limestone contained in the water used for diluting the composition prior to use. By way of non limiting example the sequestering agent is EDTA or still Nitrilo Triacetil acid, an excellent sequestering agent of calcium contained in water.

The present invention may form part of a global health program for a cattle raising facility during which the building and the material therein are in depth cleaned using an appropriate detergent, then disinfected and rinsed.

The composition according to the invention is then applied, in particular at a concentration between 4 and 20% by weight over all the surfaces of the livestock building: floors, walls, ceilings and equipment.

The composition is then applied at the concentration enabling elimination of the oocysts. This concentration may vary from one building to the other, in particular depending on its configuration and the severity of the infection.

By way of example, good results were obtained by using the composition presenting the following formulation in weight ratios:
 water—37.2%
 triamine—38.4%
 quaternary ammonium—5%,
 a surfactant—14.6%,
 a sequestering agent—4.8%

In this example, the triamine may be dodecyl-dipropylenetriamine, the quaternary ammonium derivative may be N—($C_{8-18}$-alkyl-N-benzyl-N,N-dimethylammonium chloride, the surfactant may be ethoxylated alcohol of C12-C15 (+11 E.O) type and the sequestering agent Nitrilo Triacetil Acid.

More generally, the composition may exhibit a formulation in weight ratios comprising:
 triamine between 20% and 60%,
 quaternary ammonium between 0% and 10%,
 a surfactant between 0.5% and 30%,
 a sequestering agent between 0% and 10%,
 water up to 100%,
the sum of the percentages totaling 100%.

In the present invention, the keratolytic activity of the composition was measured using the official German protocol of the DVG. This test has been set up so as to assess the efficiency of alkylamines on coccidia. Alkylamine is preferably formulated in the form of a solution so as to conduct the efficiency assessment test described below. Preferably, it will be an aqueous solution.

The in-vivo protocole was conducted to the guidelines release 2000 of the DVG German protocol (Guidelines for the testing of chemical disinfectants against coccida oocysts).

The infection power of an inoculum of disinfected oocysts may be calculated from the infectious dose and the inoculated dose according to the following equation:

infection power [%]=infectious dose×100/inoculated dose the efficiency of the disinfectant is expressed in % of non-infectious oocysts: efficiency [%]=100−infection power [%].

In order to demonstrate the efficiency of the composition as described in the present invention, the test composition, designated composition 1, in the table of FIG. 2, as well as a phenol-based commercial product, were tested and compared according to the protocol presented above.

The results are presented in the table of FIG. 1 representing the count results of the controls. The results are illustrated by points in the graph of FIG. 3 representing the excreted dose in an infectious dose dependent manner.

The linear regression graph may be calculated from these points to represent the excreted dose in an infectious dose dependent manner.

The equation of the regression graph enables one to determine the infectious dose corresponding to the excretion found.

In this test, 2000 oocysts correspond to a 100%-infection ratio. The efficiency ratio of said composition 1 is presented in the table of FIG. 2 equal to 98.2%. This efficiency ratio should be compared with that of a phenol-based commercial product, i.e. 96.2%.

Said tested composition 1, based on alkylamine, hence presents an efficiency against coccidiosis oocysts according to the DVG protocol which sets the minimum efficiency ratio to 95%.

We shall describe therebelow a few tested formulations for illustrating the synergistic effect between alkylamine and quaternary ammonium.

Example 1

| % (p/p) | Water | Composition A | Composition B | Composition C |
|---|---|---|---|---|
| Water | 100 | 70 | 60 | 97.35 |
| Dodecyldipropylene-triamine | — | 30 | 40 | — |
| N-(C8.18-alkyl-N-benzyl-N,N-dimethylammonium) chloride | — | — | — | 1.25 |
| Didecyldimethylammonium chloride | — | — | — | 1.25 |
| % Reduction (4% - 2 hr) | 0 | 70.6 | 78.3 | 10.4 |

Example 2

Tests on the Type of Alkylamine

The activity of several alkylamine classes was assessed.
Concentrated mother solutions were first prepared including 30% alkylamine, 2.5% N-(C8-C18)-N-benzyl-N,N-dimethylammonium chloride, 24% amphoteric surfactants, 5% sequestering agent and water to balance to 100%.

| % (p/p) | Composition D | Composition E | Composition F |
|---|---|---|---|
| C16-22 alkylamine | 30 | — | — |
| Oleylpropylenediamine | — | 30 | — |
| Dodecyldipropylenetriamine | — | — | 30 |
| N-(C8.18-alkyl-N-benzyl-N,N-dimethylammonium) chloride | 2.5 | 2.5 | 2.5 |
| Amphoteric surfactants | 25 | 25 | 25 |
| Sequestering agent | 5 | 5 | 5 |
| % Reduction (4% - 2 hr) | 55.3 | 47.1 | 93.5 |

Example 3

Tests on Alkylamine Concentration

The table shows the effect of dodecyldipropylenetriamine concentration in a system containing 2.5% N-(C8-18-alkyl)-N-benzyl-N,N-dimethylammonium chloride, 24% amphoteric surfactants, 5% sequestering agent and water to balance to 100%.

| Dodecyldipropylenetriamine concentration | % Reduction (4% - 2 hr) |
|---|---|
| 0 | 11.2 |
| 10 | 56.8 |
| 20 | 89.1 |
| 30 | 93.5 |
| 40 | 98.0 |
| 50 | Non dispersible formula |

Example 4

The purpose of the following tests is to show the advantage of incorporating a quaternary ammonium derivative into the composition according to the invention.

The tested quaternary ammonium derivative, N-(C8-18-alkyl)-N-benzyl-N,N-dimethylammonium chloride, was incorporated into a system containing by weight 30% dodecyldipropylenetriamine, 24% amphoteric surfactants, 5% sequestering agent and water to balance to 100%.

| Concentration of N-(C8-18-alkyl)-N-benzyl-N.N-dimethylammonium chloride (%) | % Reduction (4% - 2 hr) |
|---|---|
| 0 | 75.3 |
| 2.5 | 93.5 |
| 5 | 95.3 |
| 10 | 98.6 |

We claim:

1. A method of treating surfaces of livestock buildings or material therein so as to eliminate or inhibit coccidiosis oocysts wherein the method comprises a step of applying to the surface or material a composition consisting of an alkylamine, one or more quaternary ammonium derivatives, a surfactant, a sequestering agent, and water, wherein said step of applying is performed by pulversation, thermonebulisation, or soaking of the surfaces of the livestock buildings or the material therein, and wherein the quaternary ammonium derivative is selected among the group consisting of:
   compounds of the quaternary ammonium ion, (hydrogenated tallow alkyl)trimethyls, chlorides,
   compounds of the quaternary ammonium ion, coco trimethyl alkyls, chlorides,
   compounds of the quaternary ammonium ion, coco bis (hydroxyethyl)benzyl alkyl, chlorides,
   compounds of the quaternary ammonium ion, coco dimethyl benzyl alkyl, chlorides,
   compounds of the quaternary ammonium ion, coco dimethyl dialkyls, chlorides,
   compounds of the quaternary ammonium ion, bis(hydrogenated tallow alkyl)dimethyls, chlorides,
   compounds of the quaternary ammonium ion, soya trimethyl, alkyls, chlorides,
   compounds of the quaternary ammonium ion, benzyl $C_{8-18}$ alkyl dimethyls, chlorides,
   compounds of the quaternary ammonium ion, benzyl $C_{12-18}$ alkyl dimethyls, chlorides,
   compounds of the quaternary ammonium ion, $C_{6-12}$ dialkyl dimethyls, chlorides,
   compounds of the quaternary ammonium ion, benzyl $C_{8-16}$ alkyl dimethyls, chlorides,
   compounds of the quaternary ammonium ion, benzyl $C_{12-16}$ alkyl dimethyls, chlorides,
   compounds of the quaternary ammonium ion, $C_{8-10}$ dialkyl dimethyls, chlorides,
   compounds of the quaternary ammonium ion, (oxydiethanediyl-1,2)bis[coco alkyldimethyl], dichlorides,
   compounds of the quaternary ammonium ion $C_{12-18}$ alkyl [(ethylphenyl)methyl]dimethyls, chlorides,
   compounds of the quaternary ammonium ion, benzyl $C_{10-16}$ alkyl dimethyls, chlorides,
   compounds of the quaternary ammonium ion, benzyl $C_{12-18}$ alkyl dimethyls, salt with benzisothiazol-1,2 one-3(2H)-1,1-dioxide, (1:1),
   compounds of the quaternary ammonium ion, $C_{8-18}$ dialkyl dimethyls, chlorides,
   compounds of the quaternary ammonium ion, benzyl $C_{12-14}$ alkyl dimethyls, chlorides,
   compounds of the quaternary ammonium ion, $C_{12-14}$ alkyl [(ethylphenyl)methyl]dimethyls, chlorides,
   compounds of the quaternary ammonium ion, benzyl $C_{8-18}$ alkyl dimethyls, bromides,
   compounds of the quaternary ammonium ion, [[[[(carboxy-2 ethyl)(hydroxy-2 ethyl)amino]-2 ethyl] amino]-2 oxo-2 ethyl]coco dimethyl alkyls, hydroxides, internal salts,
   N-methylmethanamine polymer (Einecs 204-697-4) with (chloromethyl)oxirane (Einecs 203-439-8)/polymerised quaternary ammonium chloride,
   quaternary ammonium iodides,
   quaternary ammonium compounds (benzylalkyldimethyl (saturated and unsaturated $C_{8-22}$ alkyls, and tallow alkyl, coco alkyl and soya alkyl) chlorides, bromides or Hydroxides/BKC,
   quaternary ammonium compounds (dialkyldimethyl (saturated an unsaturated ($C_{6-18}$ alkyls, and sulphur alkyl, coco alkyl and soya alkyl) chlorides, bromides or methyl sulphates/DDAC, and
   quaternary ammonium compounds (alkyltrimethyl (saturated and unsaturated $C_{8-18}$ alkyl, and sulphur alkyl, coco alkyl, and soya alkyl) chlorides, bromides or methyl sulphates/TMAC.

2. The method according to claim 1, wherein said alkylamine is a triamine.

3. A method of treating surfaces of livestock buildings or material therein so as to eliminate or inhibit coccidiosis oocysts wherein the method comprises a step of applying to the surface or material a composition, wherein said composition presents a formulation in weight ratio comprising:
triamine between 20% and 60%,
quaternary ammonium up to 10%,
a surfactant between 0.5% and 30%,
a sequestering agent between 0% and 10%, and
water up to 100%,
the sum of the percentages totalling 100%,
wherein said step of applying is performed by pulversation, thermonebulisation or soaking of the surfaces of the livestock buildings or the material therein, and wherein the quaternary ammonium is selected among the group consisting of:
compounds of the quaternary ammonium ion, (hydrogenated tallow alkyl)trimethyls, chlorides,
compounds of the quaternary ammonium ion, coco trimethyl alkyls, chlorides,
compounds of the quaternary ammonium ion, coco bis(hydroxyethyl)benzyl alkyl, chlorides,
compounds of the quaternary ammonium ion, coco dimethyl benzyl alkyl, chlorides,
compounds of the quaternary ammonium ion, coco dimethyl dialkyls, chlorides,
compounds of the quaternary ammonium ion, bis(hydrogenated tallow alkyl)dimethyls, chlorides,
compounds of the quaternary ammonium ion, soya trimethyl, alkyls, chlorides,
compounds of the quaternary ammonium ion, benzyl $C_{8-18}$ alkyl dimethyls, chlorides,
compounds of the quaternary ammonium ion, benzyl $C_{12-18}$ alkyl dimethyls, chlorides,
compounds of the quaternary ammonium ion, $C_{6-12}$ dialkyl dimethyls, chlorides,
compounds of the quaternary ammonium ion, benzyl $C_{8-16}$ alkyl dimethyls, chlorides,
compounds of the quaternary ammonium ion, benzyl $C_{12-16}$ alkyl dimethyls, chlorides,
compounds of the quaternary ammonium ion, $C_{8-10}$ dialkyl dimethyls, chlorides,
compounds of the quaternary ammonium ion, (oxydiethanediyl-1,2)bis[coco alkyldimethyl], dichlorides,
compounds of the quaternary ammonium ion $C_{12-18}$ alkyl [(ethylphenyl)methyl]dimethyls, chlorides,
compounds of the quaternary ammonium ion, benzyl $C_{10-16}$ alkyl dimethyls, chlorides,
compounds of the quaternary ammonium ion, benzyl $C_{12-18}$ alkyl dimethyls, salt with benzisothiazol-1,2 one-3(2H)-1,1-dioxide, (1:1),
compounds of the quaternary ammonium ion, $C_{8-18}$ dialkyl dimethyls, chlorides,
compounds of the quaternary ammonium ion, benzyl $C_{12-14}$ alkyl dimethyls, chlorides,
compounds of the quaternary ammonium ion, $C_{12-14}$ alkyl [(ethylphenyl)methyl]dimethyls, chlorides,
compounds of the quaternary ammonium ion, benzyl $C_{8-18}$ alkyl dimethyls, bromides,
compounds of the quaternary ammonium ion, [[[[(carboxy-2 ethyl)(hydroxy-2 ethyl)amino]-2 ethyl]amino]-2 oxo-2 ethyl]coco dimethyl alkyls, hydroxides, internal salts,
N-methylmethanamine polymer (Einecs 204-697-4) with (chloromethyl)oxirane (Einecs 203-439-8)/polymerised quaternary ammonium chloride,
quaternary ammonium iodides,
quaternary ammonium compounds (benzylalkyldimethyl (saturated and unsaturated $C_{8-22}$ alkyls, and tallow alkyl, coco alkyl and soya alkyl) chlorides, bromides or Hydroxides/BKC,
quaternary ammonium compounds (dialkyldimethyl (saturated an unsaturated ($C_{6-18}$ alkyls, and sulphur alkyl, coco alkyl and soya alkyl) chlorides, bromides or methyl sulphates/DDAC, and
quaternary ammonium compounds (alkyltrimethyl (saturated and unsaturated $C_{8-18}$ alkyl, and sulphur alkyl, coco alkyl, and soya alkyl) chlorides, bromides or methyl sulphates/TMAC.

4. The method according to claim 3, wherein said composition presents the following formulation in weight ratios:
water—37.2%
triamine—38.4%
quaternary ammonium—5%
a surfactant—14.6%, and
a sequestering agent—4.8%.

* * * * *